(12) United States Patent
Jäger-Waldau

(10) Patent No.: US 8,734,386 B2
(45) Date of Patent: May 27, 2014

(54) ELECTRIC BREAST MILK PUMP

(71) Applicant: Mapa GmbH, Zeven (DE)

(72) Inventor: Reinhold Jäger-Waldau, Scheeßel (DE)

(73) Assignee: MAPA GmbH, Zeven (DE)

( * ) Notice: Subject to any disclaimer, the term of this patent is extended or adjusted under 35 U.S.C. 154(b) by 0 days.

(21) Appl. No.: 13/625,564

(22) Filed: Sep. 24, 2012

(65) Prior Publication Data

US 2013/0165852 A1  Jun. 27, 2013

(30) Foreign Application Priority Data

Dec. 21, 2011  (EP) .................................... 11010131

(51) Int. Cl.
  *A61M 1/06* (2006.01)
(52) U.S. Cl.
  USPC .......................................................... 604/74
(58) Field of Classification Search
  USPC ...................... 604/73–76, 131, 151
  See application file for complete search history.

(56) References Cited

U.S. PATENT DOCUMENTS

| 6,383,163 | B1* | 5/2002 | Kelly et al. ..................... 604/74 |
| 7,713,230 | B2* | 5/2010 | Kataoka et al. ................. 604/74 |
| 2013/0053764 | A1* | 2/2013 | Jaeger-Waldau ............... 604/74 |

* cited by examiner

*Primary Examiner* — Theodore Stigell
(74) *Attorney, Agent, or Firm* — Vidas, Arrett & Steinkraus, P.A.

(57) ABSTRACT

A breast milk pump having an electric motor, a pump driven by the motor, a suction cup, an electrically activated first three-way valve in a suction line, an electrically activated second three-way valve in a pressure line, an electronic control system, which sets the electric motor into an operating mode or an idle mode depending on an activation of a switch; in the operating mode, it operates the electric motor and the electrically activated first and second three-way valves in cycles, which comprise a suction phase, in which the electric motor is switched on, the inlet of the pump is connected to the suction cup via the first three-way valve and a floater valve, the pump outlet is connected via the second three-way valve.

12 Claims, 8 Drawing Sheets

Fig. 4a  Fig. 4b  Fig. 4c
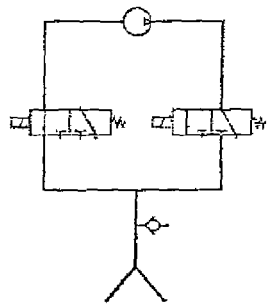
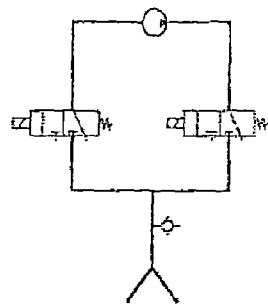
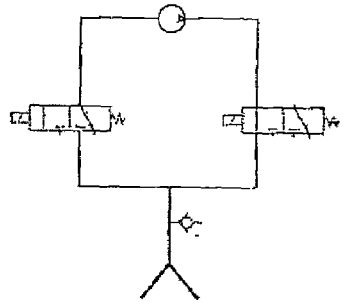
Fig. 5
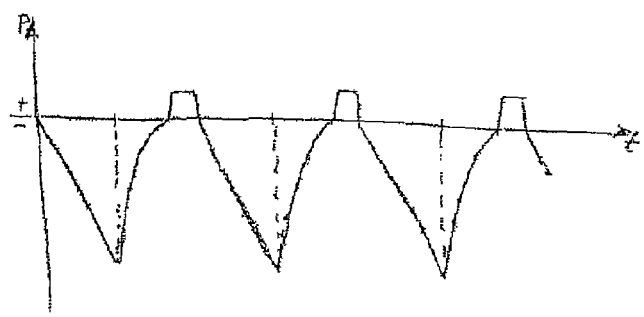

(Membrane-) pump is driven via a shaft that is driven by an electric motor.

Fig. 6a

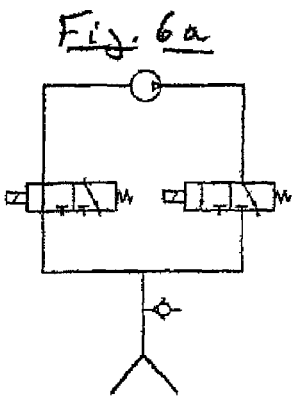

Fig. 6b

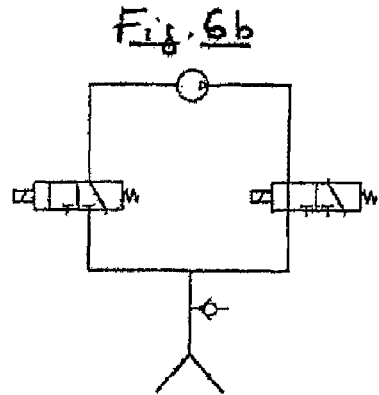

Condition „make underpressure in breastshield"

left magnet valve energized: passage
right magnet valve de-energized: closed
to breastshield, valve open to outside Condition „make overpressure in breastshield"

left magnet valve de-energized: closed
to breastshield, valve open to outside
right magnet valve energized: passage

Fig. 7a

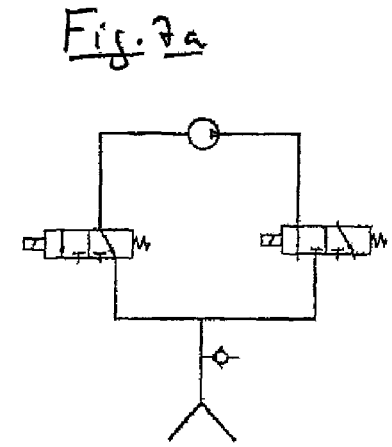

Fig. 7b

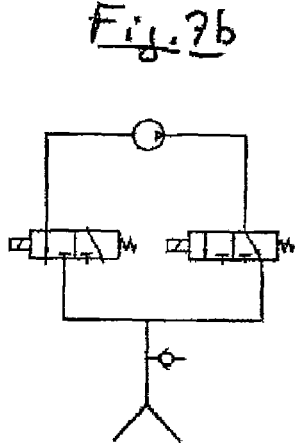

Condition „make underpressure in breastshield"

left magnet valve de-energized: passage
right magnet valve energized: closed
to breastshield, valve open to outside Condition „make overpressure in breastshield"

left magnet valve energized: closed
to breastshield, valve open to outside
right magnet valve de-energized: passage

Fig. 8a

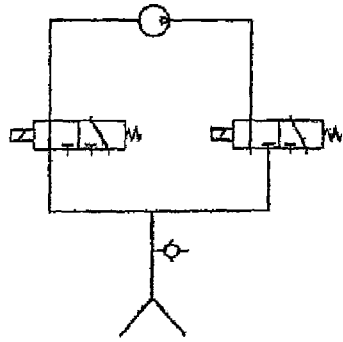

Condition „make underpressure in breastshield"

left magnet valve energized: passage
right magnet valve energized: closed
to breastshield, valve open to outside

Fig. 8b

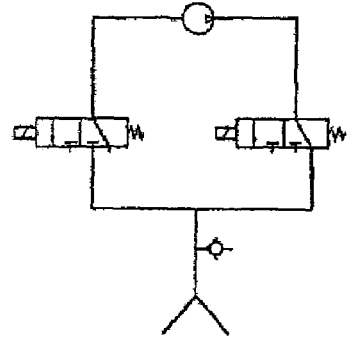

Condition „make overpressure in breastshield"

left magnet valve de-energized: closed
to breastshield, valve open to outside
right magnet valve de-energized: passage

Fig. 9a

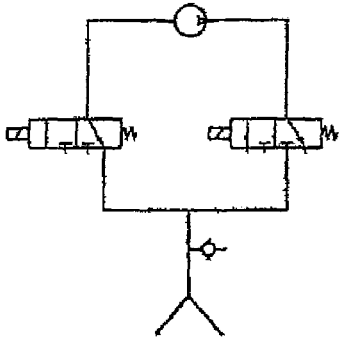

Condition „make underpressure in breastshield"

left magnet valve de-energized: passage
right magnet valve de-energized: closed
to breastshield, valve open to outside

Fig. 9b

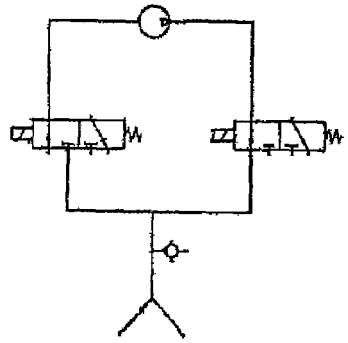

Condition „make overpressure in breastshield"

left magnet valve energized: closed
to breastshield, valve open to outside
right magnet valve energized: passage Reversely, using a solenoid valve with reverse rest position:

Fig. 10a

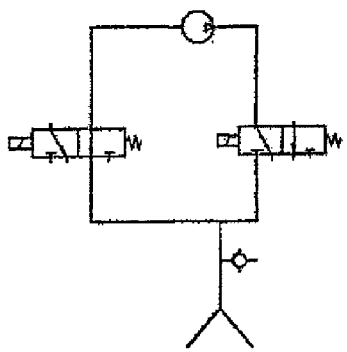

Fig. 10b

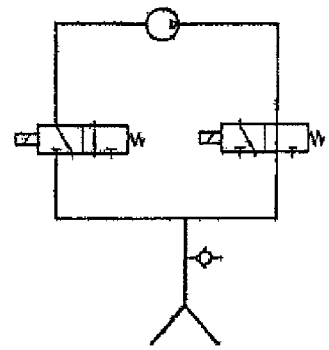

Condition „make underpressure in breastshield"

left magnet valve de-energized: passage
right magnet valve energized: closed
to breastshield, valve open to outside Condition „make overpressure in breastshield"

left magnet valve energized: closed
to breastshield, valve open to outside
right magnet valve de-energized: passage

Fig. 11a

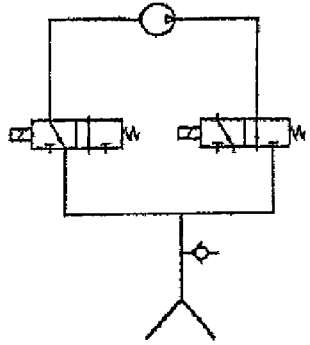

Fig. 11b

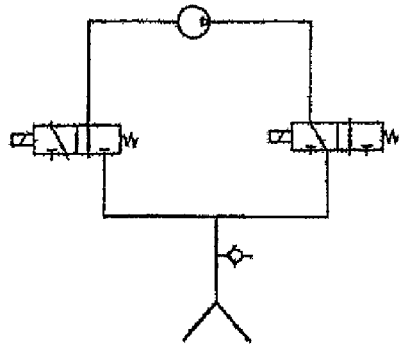

Condition „make underpressure in breastshield"

left magnet valve energized: passage
right magnet valve de-energized: closed
to breastshield, valve open to outside Condition „make overpressure in breastshield"

left magnet valve de-energized: closed
to breastshield, valve open to outside
right magnet valve energized: passage Utilization of solenoid valves having different rest positions:

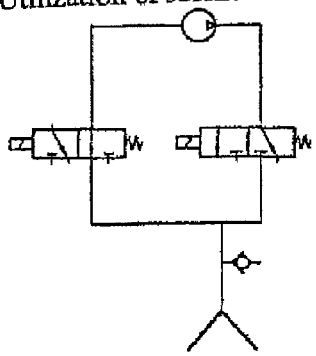

Fig. 12a

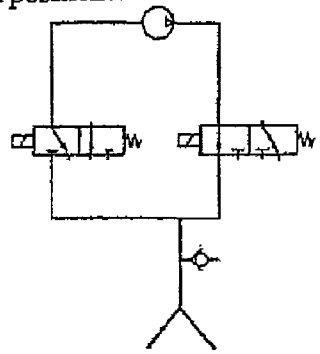

Fig. 12b

Condition „make underpressure in breastshield"

left magnet valve de-energized: passage
right magnet valve de-energized: closed
to breastshield, valve open to outside Condition „make overpressure in breastshield"

left magnet valve energized: closed
to breastshield, valve open to outside
right magnet valve energized: passage Utilization of solenoid valves having different rest positions, but reverse action direction than before:

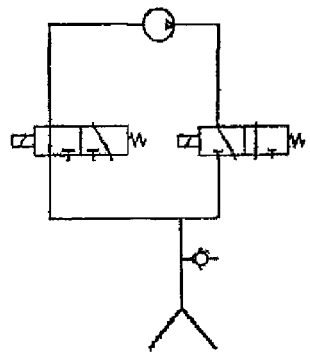

Fig. 13a

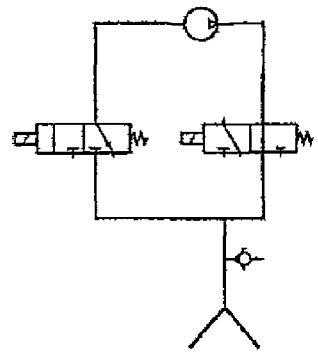

Fig. 13b

Condition „make underpressure in breastshield"

left magnet valve energized: passage
right magnet valve energized: closed
to breastshield, valve open to outside Condition „make overpressure in breastshield"

left magnet valve de-energized: closed
to breastshield, valve open to outside
right magnet valve de-energized: passage

ELECTRIC BREAST MILK PUMP

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention relates to an electric breast milk pump.

Breast milk pumps serve for pumping away breast milk. For this purpose, they have at least one suction cup, which is set onto the mother's breast. An underpressure is applied to the suction cup in order to withdraw the milk from the mother's breast. This underpressure will also be designated as "suction underpressure" in the following. The suction cup is connected to a reservoir, which receives the breast milk that is suck off. The underpressure is generated by means of a pump, which is driven manually or by means of an electric motor. Electric breast milk pumps driven by means of an electric motor are known, which have an electronic control system which controls certain pumping sequences. In these pumping sequences, the pump is switched on and off during defined periods in order to stimulate the flow of milk. The magnitude of the negative pressure (called underpressure in the following) can be adjusted.

From WO 2011/137994 A, the entire contents of which is incorporated herein by reference, an electric breast milk pump is known which has a pump driven by an electric motor, which is connected via a suction line to a floater valve chamber, which is connected to a suction cup via a connection channel. At the lower end of the connection channel, there is arranged a milk outlet valve in the form of a duckbill valve with a valve slit at the lower end. Suction cup, connection channel and underpressure chamber are disposed on a threaded ring, which can be screwed to a vented reservoir for collecting milk, so that the duckbill valve projects into the milk bottle. A floater body is disposed in the floater valve chamber, which floats up as soon as an excessive amount of milk is accumulated in the chamber. The floated-up floater body closes the connection to the pump, so that the milk does not arrive in the pump and clog or respectively agglutinate it. The suction line is connected to the surroundings (the atmosphere) via a venting line, in which an electrically activated venting valve is disposed. An electronic control system controls the operation of the pump. When the pump runs, the control system closes the venting valve, so that an underpressure is generated in the underpressure chamber and milk is suck off. The sucked milk flows through the connection channel to the duckbill valve. The duckbill valve provides that the underpressure in the suction cup is maintained.

In order to stimulate the milk flow, the pump is cyclically switched on and off by the control system. In the switched off phases, the venting valve is opened, so that the underpressure in the suction cup is reduced. The milk flow is stimulated by these pressure variations. For instance, the pump is switched on and off 30 times per second. The milk accumulates above the duckbill valve and drops into the reservoir via the slit when the venting valve is opened.

It has proven that milk can be aspirated into the pump in spite of the floater valve. In particular, this happens at short venting phases or high milk flows, respectively. When the pump aspirates milk, the valves or respectively the membrane of a membrane pump can agglutinate, which can lead to smaller suction efficiency or to the breakdown of the pump, respectively.

The document EP 1 221 319 B1, the entire contents of which is incorporated herein by reference, describes a breast pump with a membrane exhauster having a drive motor and control electronics for adjusting the motor speed depending on a pre-programmed course of the vacuum. A vacuum chamber with separating membrane is provided in addition, whose first chamber separated by the separating membrane is connected to the suction line of the exhauster, and whose second chamber separated by the separating membrane can be connected to a suction hood. The separating membrane prevents milk from entering the exhauster.

In this breast pump, an underpressure is applied to the breast according to a program, in order to stimulate the milk efficiency. Amount and frequency of the underpressure in particular are controlled by the program. A particularly advantageous sucking program is in every cycle to build up the desired vacuum progressively, and to maintain the maximum vacuum during a predetermined period of time, and subsequently to decrease the vacuum to zero vacuum as promptly as possible, in order to perform the following cycle after a rest. For this reason, the breast pump is equipped with a controlled device for nullifying the vacuum that has been built up. The device for nullifying the vacuum consists of a valve controlled by the control electronics, which connects the first chamber to the surroundings when it is opened, i.e., vents the vacuum chamber passively. Alternatively, the device for nullifying the vacuum in the vacuum chamber consists of a valve switch, which interrupts the suction line between the exhauster and the first chamber when it is activated, and connects the first chamber with an ejection line of the exhauster, which builds up a positive pressure instead, that is to say, nullifies the vacuum in the vacuum chamber in an active manner by building up a positive pressure.

Starting from this, the present invention is based on the task to provide an electric breast milk pump which is better protected against aspiration of milk through the pump.

The electric breast milk pump according to the present invention has:
an electric motor,
a pump driven by the electric motor,
at least one suction cup,
a breast milk outlet, connected to the suction cup via a connection channel,
a reservoir for collecting breast milk, connected to the outlet,
an outlet valve disposed in the outlet, which closes when the difference between the pressure in the reservoir and that in the suction cup has a certain minimum value, and which opens when the value has fallen below the minimum,
a floater valve chamber which is connected to the connection channel at the downside, and has a passage opening and a seal seat surrounding the passage opening at the topside,
a floater body, disposed in the floater valve chamber, which has a sealing body at the topside which bears sealingly against the seal seat when the floater body floats up in the floater valve chamber,
a suction line, connecting the passage opening to the inlet of the pump,
an electrically activated first three-way valve, disposed in the suction line, a pressure line, connected to the connection channel and the outlet of the pump, an electrically activated second three-way valve, disposed in the pressure line, switch mechanism for switching the electric motor on and off, and an electronic control system, which is electrically connected to the switch mechanism, the electric motor and the electrically activated first and second three-way valves, and which is configured to set the electric motor into an operating mode or an idle mode depending on an activation of the switch mechanism, wherein in the operating mode, it operates the electric motor and the electrically activated first and second three-way valves in cycles, which comprise a suction phase, in which the electric motor is switched on, the inlet of the pump is connected to the passage opening via the suction line and the first three-way valve, and the outlet of the pump is connected to the surroundings via the pressure line and the second three-way valve and which further comprise a pressure phase, in which the electric motor is switched on, the inlet of the pump is connected to the surroundings via the suction line and the first three-way valve and the outlet of the pump is connected to the connection channel via the pressure line and the second three-way valve.

BRIEF SUMMARY OF THE INVENTION

The present invention is based on the finding that in the known breast milk pump with electronically controlled venting valve, the pressure compensation in the suction cup does not occur quickly enough in the venting phases at short cycles or high milk flows, respectively, so that the milk pumped off does not or not sufficiently flow away into the reservoir via the outlet valve. As a consequence, it can occur that the milk gradually jams above the outlet valve, rises up to the seal seat of the floater valve and arrives in the interior of the pump. This can happen with small breast milk pumps in particular, in which the venting line and the venting valve have small dimensions, whereby the flow in the pressure compensation is limited. According to the present invention, this problem is overcome in that in the operating mode, air is actively pumped into the connection channel, and thus into the suction cup and the outlet in the pressure phases, so that the pressure above the outlet valve can be brought to the surroundings pressure, or even to a small overpressure with respect to the surroundings pressure, more quickly than with passive venting. The outlet valve opens through the increased pressure above the outlet valve. As a consequence, the milk pumped off in the suction phases and standing above the outlet valve can flow down with sufficient speed into the reservoir through the outlet valve between the suction phases, and does not rise up to the valve seat of the floater valve. The milk flows off particularly quickly when a small overpressure against the surroundings pressure is set in the connection channel. The period of time for actively pumping air into the connection channel can be shorter than the span between two consecutive suction phases. In the remaining time between two suction phases, the electric motor can be switched off in order to save energy and to reduce the motor's wear. In the idle mode, the electric motor is also switched off.

According to one embodiment, the electronic control system is configured such that the electric motor is switched off in a venting phase subsequent to the pressure phase or between the suction phase and the pressure phase, the inlet of the pump is connected to the surroundings (the atmosphere) via the suction line and the first three-way valve, and the outlet of the pump is connected to the connection channel via the pressure line and the second three-way valve. Partial or complete pressure compensation with the surroundings takes place in the venting phase by passive venting of the suction cup across the pump. The venting phase may follow up after the pressure phase, so that the accumulated milk is safely discharged into the reservoir after the suction phase at first. Instead, the venting phase can follow up directly after the suction phase, and by a pressure phase subsequent to the venting phase, it can be made sure that the accumulated milk drains off into the reservoir. When the venting phase is subsequent to the pressure phase, the electric motor can continue to run in the transition from the suction phase to the pressure phase, and only the three-way valves have to be switched over. When the venting phase is subsequent to the suction phase, the electric motor can continue to run in the transition from the pressure phase to the next suction phase, wherein the three-way valves must be switched over.

According to another embodiment, the electronic control system is configured such that in a venting phase between the suction phase and the pressure phase, it connects the inlet of the pump via the suction line and the first three-way valve and the outlet of the pump via the pressure line and the second three-way valve to the surroundings. In this embodiment, gradual pressure compensation with the surroundings takes place in the venting phase by inevitably existing leaks.

According to one embodiment, there are means for adjusting the speed of the electric motor, and the electronic control system is configured such that it operates the electric motor with a speed according to the setting of the means for adjusting the speed. Through this, the suction underpressure generated by the pump can be adjusted according to requirements. Compared to breast milk pumps in which the suction underpressure can be adjusted by means of a permanent, adjustable venting, less electric energy is required and the wear of the electric motor is reduced. According to a further embodiment, the electronic control system is configured such that it operates the electric motor continuously or in cycles according to the setting of the means for adjusting. Depending on the requirements of the user, the pump can work continuously or in cycles with suction- and pressure phases, and as the case may be, with venting phases.

According to a further embodiment, the first three-way valve and/or the second three-way valve is a three/two-way valve. In this, it is dealt with a special three-way valve, which has two valve positions. In principle, the three-way valve can also have more than two valve positions. Further, a valve can be used as the three-way valve, in which more than two flow paths can be opened and closed, from which only two openable and closable flow paths are used in the context of the present invention.

According to a further embodiment, the first three-way valve and/or the second three-way valve is an electromagnetic valve. Further preferred, the electromagnetic valve is a solenoid valve. But the utilisation other electrically activated valves is also possible, for instance of a valve actuated by a piezo drive.

According to a further embodiment, the suction cup is connected to the surroundings via a pressure relief valve. The pressure relief valve permits pressure compensation with the pressure of the surroundings when there is an excessive pressure in the suction cup.

Of course, the breast milk pump has a power supply, which feeds the electric motor, the first and the second three-way valve and the electromagnetic control system. In this, it can be dealt with a battery, an accumulator, a charger or respectively a mains adapter in particular. Combinations of the mentioned power supplies are possible.

According to one embodiment, the electric motor is a DC motor with brush and commutator. Such motors, which are designed for a working life of some 100 hours of function, are available in a compact construction and with suitable power dimensions.

According to one embodiment, the electromagnetic control system has a printed circuit board with a micro computer, in which one or several programs for controlling the electric motor as well as the first and the second three-way valve are stored. Different programs can be selectable by placing jumpers at different positions of the printed circuit board at option. The jumpers connect strip conductors of the printed circuit board, which are connected to the micro computer. According to which strip conductors are connected, the micro computer is operated in different switching conditions wherein it performs different programs. By setting the jumpers, it is possible to select desired programs of the pump in its production. Through this, a family of breast milk pumps with different pumping sequences can be provided. Only the variable attachment of jumpers is necessary for this. The jumpers may be wire bridges that are soldered into the printed circuit board.

According to a further embodiment, the pump is a membrane pump. By means of a membrane pump, the necessary suction underpressures can be built up in a short time with compact construction. The suction underpressures are preferably in the range of 330 to 50 mbar. In the suction phases, these suction underpressures can be built up by means of a membrane pump within a time in the range of seconds, or even below. Instead of a membrane pump, a reciprocating pump or a hose pump can be used in particular.

According to a further embodiment, the outlet valve is a duckbill valve. A duckbill valve is valve having a V-shaped cross section, with a slit at the contact line between the legs of the V. The duckbill valve closes when the difference of the pressures present below and above the legs reaches a certain minimum value, and it opens when this difference falls below the minimum value. The pressure above the outlet valve is determined by the amount of the liquid standing over it, and by the suction underpressure or the overpressure applied by the pump or the surrounding pressure. At vented reservoir, the pressure below the outlet valve is the surrounding pressure. Arbitrary other mechanical nonreturn valves can also be used instead of a duckbill valve.

According to a further embodiment, the breast milk pump has a lid detachably connected to the reservoir, on which the suction cup, the connection channel, the floater valve chamber and the outlet with the outlet valve are disposed. The lid is preferably a screwable lid with a screw thread, which can be screwed to a complementary thread on the edge of the reservoir.

The lid has preferably a venting channel for venting the reservoir on which the lid is fixed.

According to a further embodiment, the suction cup, the connection channel, the outlet and the floater casing are connected to the lid in one piece.

According to a further embodiment, the electric motor, the pump, the electronic control system, the second three-way valve and a power supply are combined in one casing.

BRIEF DESCRIPTION OF THE SEVERAL VIEWS OF THE DRAWINGS

In the following, the present invention will be explained in more detail by way of the attached drawings of examples of its realisation. In the drawings show:

FIGS. 4a to 4c a pneumatic connection scheme of a breast milk pump with position of the three-way valves in the suction phase (FIG. 4a), in the venting phase with pressure compensation through leaks (FIG. 4b) and in the pressure phase (FIG. 4c);

FIG. 5 the course of pressure over time in a mode of operation in which a venting phase with pressure compensation through leaks follows after each suction phase, and a pressure phase follows after the venting phase.

FIGS. 6a to 13a and 6b to 13b variants of the pneumatic connection scheme of the breast milk pump with the position of the three-way valves in the suction phase (FIGS. 6a to 13a) and with the position of the three-way valves in the pressure phase (FIGS. 6b to 13b).

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Figure 1A:
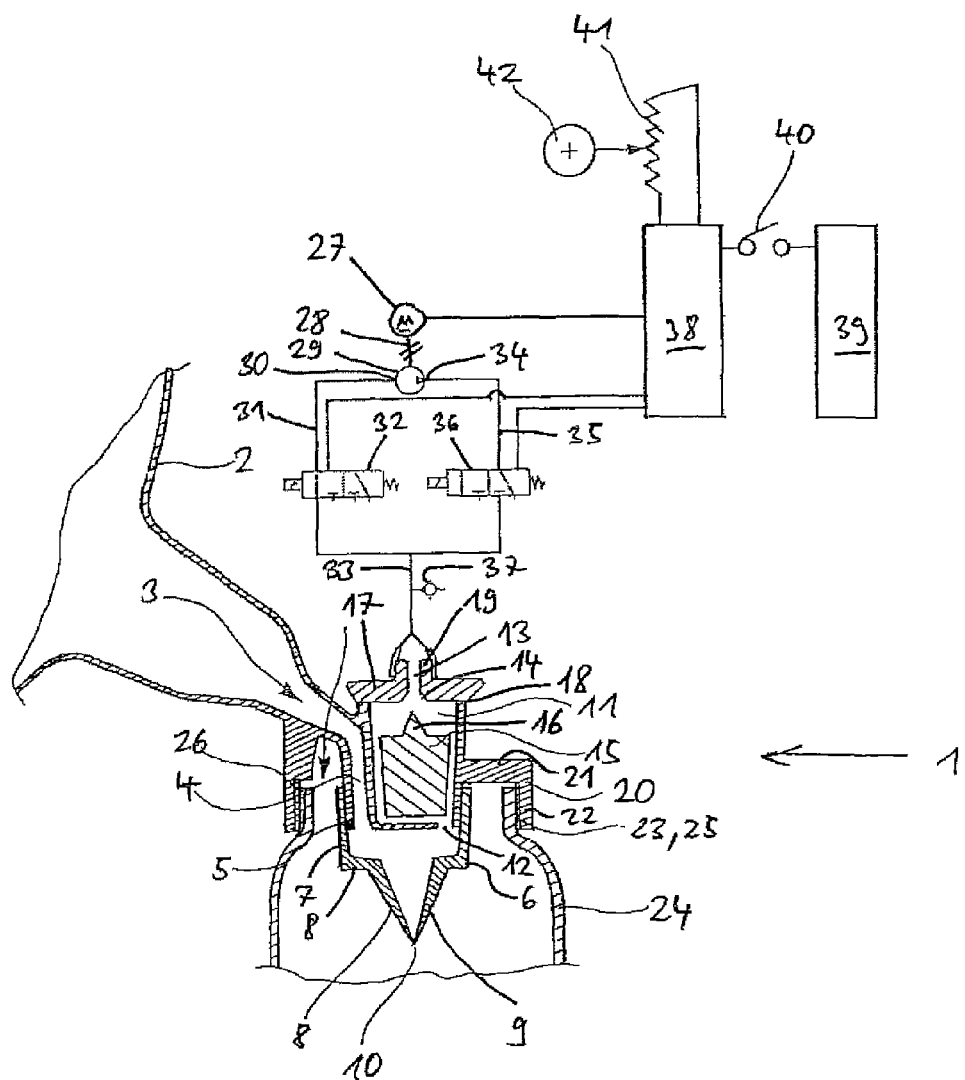
FIG. 1a and 1b a breast milk pump of the present invention in a rough schematic vertical section with associated pneumatic and electronic circuitry in the suction phase (FIG. 1a) and in the pressure phase (FIG. 1b)
Figure 1B:
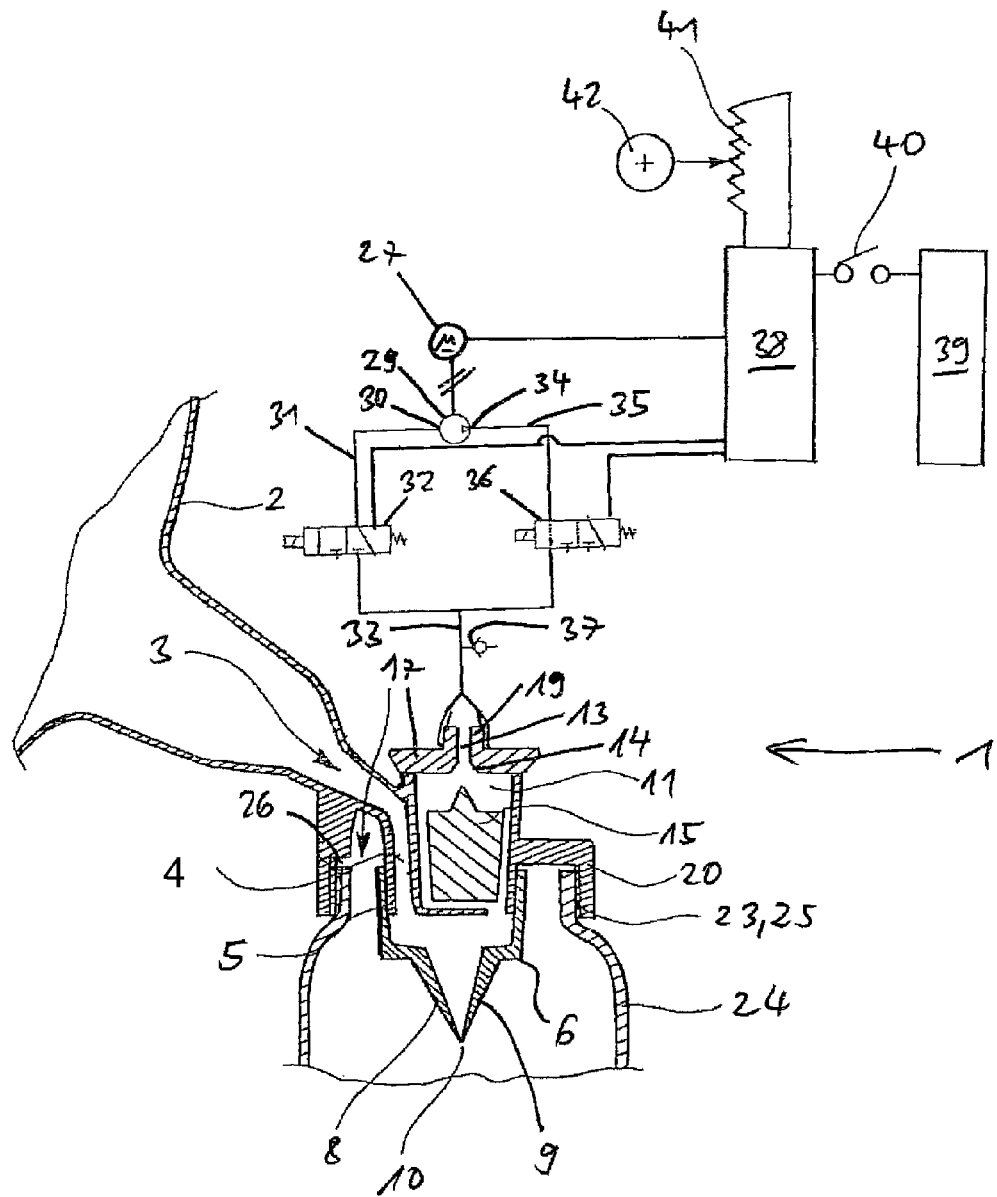

According to FIGS. 1a and 1b, a breast milk pump 1 has a suction cup 2, which broadens towards the outside and has an opening 3 to a connection channel 4 at its inner end. At the lower end, the connection channel 4 merges into an outlet 5 in the form of a vertically directed pipe neck.

On the outlet 5 sits a discharge valve 6 in the form of a duckbill valve. The duckbill valve 6 is made of an elastic and inert material, for instance of silicone rubber or latex. At its upside, the duckbill valve 6 has a pipe-shaped portion 7, which has a valve bottom 8a at the downside, from which two flat legs 8, 9 project towards the downside. The duckbill valve 6 is clamped onto the pipe neck with its pipe-shaped portion. The legs 8, 9 are inclined towards each other, and there is a valve slit 10 between their lower ends.

Further, the breast milk pump 1 has a cylindrical or conical floater valve chamber 11, which is oriented vertically. The floater valve chamber 11 is connected to the connection channel 4 at its downside, via a connection opening 12. At the topside, the floater valve chamber 11 has a passage opening 13, around which there is a conical seal seat 14.

A floater body 15 is arranged in the floater valve chamber 11, whose outer shape is matched to the interior space the floater valve chamber 11 so that it can float up in the floater valve chamber 11. The floater body 11 has a conical sealing body 16 centrally at its upside, which has a shape complementary to the seal set 14.

The passage opening 13 is formed in a chamber lid 17 of the floater valve chamber 11, which is detachably or permanently closed via a plastics welding connection 18 after the insertion of the floater body 15. At the topside, the chamber lid 17 has a fitting piece 19, into which the passage opening 13 opens.

The suction cup 2, the connection channel 4, the outlet 5 and the floater valve chamber 11 are integrally connected to a lid 20, which is configured as a screw lid. For this purpose, the lid 20 has a lid bottom 21 and a cylindrical lid shell 22, which is provided with an internal thread 23 at its inner circumference.

Further, the breast milk pump has a reservoir 24, which has an external thread 25 at the outer circumference of the reservoir opening, to which the lid 20 is screwed.

The lid 20 has a venting channel 26, which opens at its one end into an inner surface at the inner side of the lid 20 facing the inner space of the reservoir 24, and at its other end into an outer surface of the lid 20 facing the surroundings.

Further, the breast milk pump 1 has an electric motor 27, configured as a DC motor with brushes and commutator. The electric motor 27 is coupled via a shaft 28 to a pump 29, which is configured as a membrane pump. A suction line 31 is connected to the inlet 30 of the pump 29, in which a first, electrically controllable three/two-way valve 32 is arranged. At its other end, the suction line 31 is connected to the fitting piece 19 via a header pipe 33.

A pressure line 35 is connected to the outlet 34 of the pump 29, in which a second, electrically controllable three/two-way valve 36 is arranged. At its other end, the pressure line 35 is connected to the fitting piece 19 via the header pipe 33.

A pressure relief valve 37 is connected to the header pipe 33 and opens into the surroundings.

The first and second three/two-way valves 32, 36 each have a switch position in which they open into the surroundings (i.e., into the atmosphere).

Further, the breast milk pump 1 comprises an electronic control system 38 and a supply 39 for electric current. The supply 39 for electric current provides the electronic control system 38, the electric motor 27 and the electrically switchable first and second three/two-way valves 32, 36 with current.

The electronic control system 38 is connected to an on-off switch 40 and means 41 for adjusting the speed of the electric motor, which have a small adjustment wheel 42.

The electronic control system 38 is electrically connected to the electric motor 27 and the electrically activated first and second three-way valves 32, 36.

By activating the on-off switch 40, the breast milk pump 1 can be switched on and off. The switched-on condition of the breast milk pump 1 is designated as the operating mode, and the switched-off condition as the idle mode.

In the operating mode, the electronic control system 38 controls the speed of the electric motor 27 according to the pump speed set by way of the means for adjusting 41.

Further, the electronic control system 38 controls the electric motor 27 and the first and second three/two-way valves 32, 36 in regularly repeating cycles. Each cycle comprises at least one suction phase and one pressure phase. As the case may be, the cycle comprises also a venting phase.

The first and second three-way valves 32, 36 are controlled magnetically.

The switching position of the three/two-way valves 32, 36 in the suction phase is depicted in FIG. 1a. Here, the first three/two-way valve 32 is energized, and the second three/two-way valve 36 is de-energized.

The first three/two-way valve 32 is switched for passage, so that the inlet 30 of the pump 29 is connected to the outlet 5 via the suction line 31, the header pipe 33, the passage opening 13 and the floater valve chamber 11. The second three/two-way valve 36 is connected to the surroundings, so that the outlet 34 of the pump 29 is connected to the surroundings via the pressure line 35 and the valve 36. As a consequence, the pump 29 conveys air out of the suction cup 2 across the floater valve chamber 11. Due to the underpressure, milk is pumped off, which flows down to the outlet valve 6 and accumulates there. The air pumped off is discharged into the surroundings by the pump 29.

According to FIG. 1b, the first three/two-way valve 32 is de-energized and connected to the surroundings, and the second three/two-way valve 36 is energized and switched for passage in the pressure phase. As a consequence, the inlet 30 of the pump 29 is connected to the surroundings via the suction line 31, and the outlet 34 of the pump is communicatingly connected to the suction cup 2. As a consequence, air from the surroundings is conveyed by the pump 29 into the floater valve chamber 11, and through this into the connection channel 4 and into the outlet 5 above the duckbill valve 6. Through this, pressure compensation with the pressure of the surroundings, or even an overpressure against the pressure of the surroundings is quickly achieved there. As a consequence, the duckbill valve 6 opens promptly, and the accumulated milk flows down into the reservoir 24 in a sufficient extent.

A further suction phase may immediately follow after the pressure phase. But it is also possible that a venting phase follows before or after the pressure phase, in which the connection channel 4 is not vented actively but passively.

In order to vent in a venting phase, just only the electric motor 27 is switched off. In the switching position of the valves in FIG. 1b, air flows into the connection channel 4 via the suction line 31, the pump 29, the pressure line 35, the header pipe 33 and the floater valve chamber 11, or out of it in the reverse order, in case that there is an overpressure in the suction cup 2.

Figure 2:
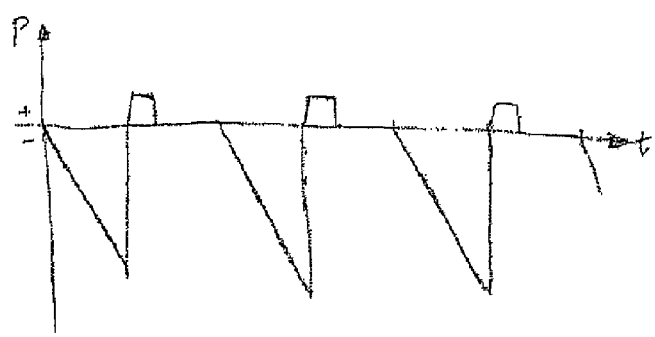
FIG. 2 the course of pressure over time in a mode of operation of the breast milk pump, in which a pressure phase follows up each suction phase, and thereafter a venting phase.

According to FIG. 2, an underpressure is generated in the suction cup 2 at running electric motor 27 in a suction phase. In this, the first and second three/two-way valves 32, 36 are switched such that the pump 29 withdraws air from the suction cup 2 and discharges it into the surroundings. In the subsequent pressure phase, air is actively pumped into the suction cup 2 at running electric motor 27. For this purpose, the three/two-way valves 32, 36 are switched over, so that the pump 29 pumps air of the surroundings into the suction cup 2. The pressure phase is ended by switching off the electric motor 27, when the overpressure was on the outlet 6 for sufficient time to give the milk off into the reservoir 24. In the subsequent venting phase, the suction cup 2 is connected to the surroundings via the electric motor 27 at unchanged valve position, so that pressure compensation with the surroundings takes place.

Figure 3:
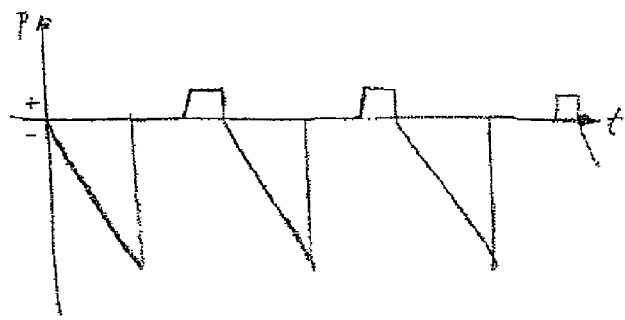
FIG. 3 the course of pressure over time in a further mode of operation of the breast milk pump, in which a venting phase follows up each suction phase, and a pressure phase follows up the venting phase.

According to FIG. 3, a venting phase follows after the suction phase. In the transition from the suction phase into the venting phase, the pump 29 is switched off and the three/two-way valves 32, 36 are switched over such that air can flow into the suction cup 2 via the pump 29. Through this, the pressure in the suction cup 2 gradually matches that of the surroundings. Subsequently, a pressure phase is performed just only by switching on the electric motor 27. Air is conveyed from the surroundings into the suction cup 2 at unchanged valve position, whereby milk or residual milk is forced to flow down into the reservoir 24 via the outlet valve 6.

FIG. 4 shows a further pneumatic configuration, in which it is worked with a venting phase. According to FIG. 4a, an underpressure is generated in the suction cup 2 in a suction phase. For this purpose, the first three/two-way valve 32 is switched to passage, so that the inlet 30 of the pump 29 is communicatingly connected to the suction cup 2. The second three/two-way valve 36 is opened towards the surroundings, so that the outlet of the pump 29 is communicatingly connected to the surroundings.

In a subsequent venting phase, the electric motor 27 is switched off or can also remain switched on. In the venting phase, the first and the second three/two-way valve 32, 36 are switched such that they are opened towards the surroundings. As a consequence, the inlet 30 and the outlet 34 of the pump 29 are communicatingly connected to the surroundings. The suction line 31 and the pressure line 35 are closed towards the suction cup 2. Due to leaks, the pressure in the suction cup 2 is gradually decreasing anyway. The shorter the venting phase is, the less the underpressure is reduced. Due to the slow reduction of the underpressure, the milk accumulated above the outlet valve 6 is not completely discharged into the reservoir 24.

According to FIG. 4c, the electric motor 27 is switched on in a subsequent venting phase, and the second three/three-way valve 36 is switched over, so that the outlet of the pump 29 is communicatingly connected to the suction cup 2. As a consequence, an overpressure is built up in the suction cup 2, which makes the milk run down into the reservoir 24 via the outlet valve 6.

Other variants of the pneumatic configuration are shown in FIGS. 6a and 6b to 13a and 13b.

According to FIG. 6a, the first three/two-way valve 32 is energized and is switched into passage condition. The second three/two-way valve 36 is de-energized, so that it is closed towards the suction cup 2 and opened towards the surroundings. In this condition, underpressure is generated in the suction cup 2 at running electric motor 27.

According to FIG. 6b, the first three/two-way valve 32 is de-energized, so that it is opened towards the surroundings and closed towards suction cup 2. The second three/two-way valve 36 is energized and is switched into passage to the suction cup 2. In this condition, air is pumped into the suction cup 2 at running electric motor 27.

According to FIG. 7a, the first three/two-way valve 32 is de-energized and is switched into passage to the suction cup 2. The second three/two-way valve 36 is energized and is closed towards the suction cup 2 and opened towards the surroundings. In this condition, underpressure is generated in the suction cup 2 at running electric motor 27.

According to FIG. 7b, the first three/two-way valve 32 is energized so that it is closed towards the suction cup 2 and opened towards the surroundings. The second three/two-way valve 36 is de-energized, so that it is switched into passage towards the suction cup 2. In this condition, air is pumped into the suction cup 2 at running electric motor 27.

According to FIG. 8a, the first three/two-way valve 32 is energized and switched into passage to the suction cup 2. The second three/two-way valve 36 is also energized, so that it is closed towards the suction cup 2 and opened towards the surroundings. In this condition, underpressure is generated in the suction cup 2 at running electric motor 27.

According to FIG. 8b, the first three-way valve 32 is de-energized, so that it is closed towards the suction cup 2 and opened towards the surroundings. The second three-way valve 36 is also de-energized, so that it is switched into passage towards the suction cup 2. In this condition, air is conveyed into the suction cup 2 at running electric motor 27.

According to FIG. 9a, the first three/two-way valve 32 is de-energized and switched into passage to the suction cup 2. The second three/two-way valve 36 is de-energized, so that it is closed towards the suction cup 2 and opened towards the surroundings. In this condition, underpressure is generated in the suction cup 2 at running electric motor 27.

According to FIG. 9b, the first three/two-way valve 32 is energized, so that it is closed towards the suction cup 2 and opened towards the surroundings. The second three/two-way valve 36 is energized, so that it is switched into passage towards the suction cup 2. In this condition, air is conveyed into the suction cup 2 at running electric motor 27.

According to FIG. 10a, the first three/two-way valve 32 is de-energized and is switched into passage to the suction cup 2. The second three/two-way valve 36 is energized, so that it is closed towards the suction cup 2 and opened towards the surroundings. In this condition, underpressure is generated in the suction cup 2 at running electric motor 27.

According to FIG. 10b, the first three/two-way valve 32 is energized, so that it is closed towards the suction cup 2 and opened towards the surroundings. The second three/two-way valve 36 is de-energized, so that it is switched into passage towards the suction cup 2. In this condition, air is conveyed into the suction cup 2 at running electric motor 27.

According to FIG. 11a, the first three/two-way valve 32 is energized and is switched into passage to the suction cup 2. The second three/two-way valve 36 is de-energized, so that it is closed towards the suction cup 2 and opened towards the surroundings. In this condition, underpressure is generated in the suction cup 2 at running electric motor 27.

According to FIG. 11b, the first three/two-way valve 32 is de-energized, so that it is closed towards the suction cup 2 and opened towards the surroundings. The second three/two-way valve 36 is energized, so that it is switched into passage towards the suction cup 2. In this condition, air is conveyed into the suction cup 2 at running electric motor 27.

According to FIG. 12a, the first three/two-way valve 32 is de-energized, so that it is switched into passage to the suction cup 2. The second three/two-way valve 36 is de-energized, so that it is closed towards the suction cup 2 and opened towards the surroundings. In this condition, underpressure is generated in the suction cup 2 at running electric motor 27.

According to FIG. 12b, the first three/two-way valve 32 is energized, so that it is closed towards the suction cup 2 and opened towards the surroundings. The second three/two-way valve 36 is energized, so that it is switched into passage towards the suction cup 2. In this condition, air is conveyed into the suction cup 2.

According to FIG. 13a, the first three/two-way valve 32 is energized, so that it is switched into passage to the suction cup 2. The second three/two-way valve 36 is also energized, so that it is closed towards the suction cup 2 and opened towards the surroundings. In this condition, underpressure is generated in the suction cup 2 at running electric motor 27.

According to FIG. 13b, the first three/two-way valve 32 is de-energized, so that it is closed towards the suction cup 2 and opened towards the surroundings. The second three/two-way valve 36 is de-energized, so that it is switched into passage. In this condition, air is conveyed into the suction cup 2 at running electric motor 27.

The pneumatic configuration of the breast milk pump 1 can be selected and modified further with respect to minimum energy consumption, taking into account the duration of the suction phases, the pressure phases and as the case may the venting phases, as well as the speed of the electric motor 27 in these phases.

This completes the description of the preferred and alternate embodiments of the invention. Those skilled in the art may recognize other equivalents to the specific embodiment described herein which equivalents are intended to be encompassed by the claims attached hereto.

What is claimed is:
1. An electrical breast milk pump (1), comprising:
an electric motor (27),
a pump (29) driven by the electric motor (27),
at least one suction cup (2), an outlet (5) for breast milk, connected to the suction cup (2) via a connection channel (4), a reservoir (24) for collecting breast milk, connected to the outlet, an outlet valve (6) disposed in the outlet (4), which closes when the difference between the pressure in the reservoir (24) and that in the suction cup (2) has a certain minimum value, and which opens when the value has fallen below the minimum, a floater valve chamber (11) which is connected to the connection channel (4) at the downside, and has a passage opening (13) at the topside, as well as a seal seat (14) surrounding the passage opening (13), a floater body (15), disposed in the floater valve chamber (11), which has a sealing body (16) at the topside which bears sealingly against the seal seat (14) when the floater body (15) floats up in the floater valve chamber (11), a suction line (31), connecting the passage opening (13) to the inlet (30) of the pump (29), an electrically activated first three-way valve (32), disposed in the suction line (31), a pressure line (35), connected to the connection channel and the outlet (34) of the pump (29), an electrically activated second three-way valve (36), disposed in the pressure line (35)

a switch mechanism (40) for switching the electric motor (27) on and off, and an electronic control system (38), which is electrically connected to the switch mechanism (40), the electric motor (27) and the electrically activated first and second three-way valves (32, 36), and which is configured to set the electric motor (27) into an operating mode or an idle mode depending on an activation of the switch mechanism (40), wherein in the operating mode, it operates the electric motor (27) and the electrically activated first and second three-way valves (32, 36) in cycles, which comprise a suction phase, in which the electric motor (27) is switched on, the inlet (30) of the pump (29) is connected to the passage opening (14) via the suction line (31) and the first three-way valve (32) and the outlet (34) of the pump (29) is connected to the surroundings via the pressure line (35) and the second three-way valve (36), and which further comprise a pressure phase, in which the electric motor (27) is switched on, the inlet (30) of the pump (29) is connected to the surroundings via the suction line (31) and the first three-way valve (32) and the outlet (34) of the pump (29) is connected to the connection channel (4) via the pressure line (35) and the second three-way valve (36).

2. The breast milk pump according to claim 1, wherein the electronic control system (38) is configured such that the electric motor (27) is switched off in a venting phase subsequent to the pressure phase or between the suction phase and the pressure phase, the inlet (30) of the pump (29) is connected to the surroundings via the suction line (31) and the first three-way valve (32), and the outlet of the pump (29) is connected to the connection channel (4) via the pressure line (35) and the second three-way valve (36).

3. The breast milk pump according to claim 1, wherein the electronic control system (38) is configured such that in a venting phase between the suction phase and the pressure phase, it connects the inlet (30) of the pump (29) via the suction line (31) and the first three-way valve (32), and the outlet (34) of the pump (29) via the pressure line (35) and the second three-way valve (36) to the surroundings.

4. The breast milk pump according to claim 1, which has means (41, 42) for adjusting the speed of the electric motor (27) and wherein the electronic control system (38) is configured such that it operates the electric motor (27) with a speed according to the setting of the means (41, 42) for adjusting the speed.

5. The breast milk pump according to claim 1, wherein the electronic control system (38) is configured such that it operates the electric motor (27) continuously or in cycles according to the setting of the means (41, 42) for adjusting.

6. The breast milk pump according to claim 1, wherein the first three-way valve (32) and/or the second three-way valve (36) is a three/two-way valve.

7. The breast milk pump according to claim 1, wherein the first three-way valve (32) and/or the second three-way valve (36) is an electromagnetic valve.

8. The breast milk pump according to claim 7, wherein at least one of the first and the second three-way valve (32, 36) is a solenoid valve.

9. The breast milk pump according to claim 1, wherein the suction cup (2) is connected to the surroundings via a pressure relief valve (37).

10. The breast milk pump according to claim 1, wherein the interior of the reservoir (24) is vented.

11. The breast milk pump according to claim 1, which has a lid (20) detachably connected to the reservoir (24), on which the suction cup (2), the connection channel (4), the floater valve chamber (11) and the outlet (5) with the outlet valve (6) are disposed.

12. The breast milk pump according to claim 11, wherein the lid (20) has a venting channel (26) which extends from an inner surface of the lid (20) to an outer surface of the lid (20) in order to vent the reservoir (24).

* * * * *